(12) United States Patent
Anhalt

(10) Patent No.: US 6,633,438 B2
(45) Date of Patent: Oct. 14, 2003

(54) ENDOSCOPIC VIDEO CAMERA WITH MAGNETIC DRIVE FOCUSING

(75) Inventor: Thomas J. Anhalt, Goleta, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 0 days.

(21) Appl. No.: 10/317,352

(22) Filed: Dec. 12, 2002

(65) Prior Publication Data

US 2003/0103279 A1 Jun. 5, 2003

Related U.S. Application Data

(63) Continuation of application No. 09/836,629, filed on Apr. 17, 2001, now Pat. No. 6,522,477.

(51) Int. Cl.[7] .......................... G02B 15/14; G02B 7/02; A61B 1/00
(52) U.S. Cl. ........................ 359/694; 359/824; 600/112
(58) Field of Search ................................. 359/819, 822, 359/823, 824, 825, 826, 830, 694; 600/112, 109

(56) References Cited

U.S. PATENT DOCUMENTS

| | | | | |
|---|---|---|---|---|
| 4,519,691 A | * | 5/1985 | Yamada et al. ............. 396/144 |
| 4,643,522 A | * | 2/1987 | Takashima .................. 359/824 |
| 4,781,448 A | | 11/1988 | Chatenever et al. ........ 359/701 |
| 5,056,902 A | | 10/1991 | Chinnock et al. ........... 359/503 |
| 5,139,383 A | | 8/1992 | Polyak et al. .................. 414/3 |
| 5,359,992 A | | 11/1994 | Hori et al. ...................... 126/4 |
| 5,706,143 A | | 1/1998 | Hipp .......................... 359/824 |
| 5,836,867 A | | 11/1998 | Speier et al. ............... 600/112 |
| 5,978,161 A | | 11/1999 | Lemke ........................ 359/824 |
| 6,080,101 A | | 6/2000 | Tatsuno et al. ............. 600/112 |
| 6,099,467 A | | 8/2000 | Kehr et al. .................. 600/167 |

FOREIGN PATENT DOCUMENTS

DE 970298 9/1958

* cited by examiner

Primary Examiner—Jordan M. Schwartz
Assistant Examiner—Timothy J Thompson
(74) Attorney, Agent, or Firm—St. Onge Steward Johnston & Reens LLC

(57) ABSTRACT

The invention relates to a magnetic drive focusing device with at least one lens within a chamber and an adjuster with magnets outside the chamber. Positioned between the lens and the chamber is a second sleeve with helical guide paths. As the adjuster is moved outside the chamber, the magnetic field within the chamber causes the lens within the chamber to move. As the lens rotates, non-magnetic guides which ride in the helical guide paths force the lens to move axially within the device.

10 Claims, 10 Drawing Sheets

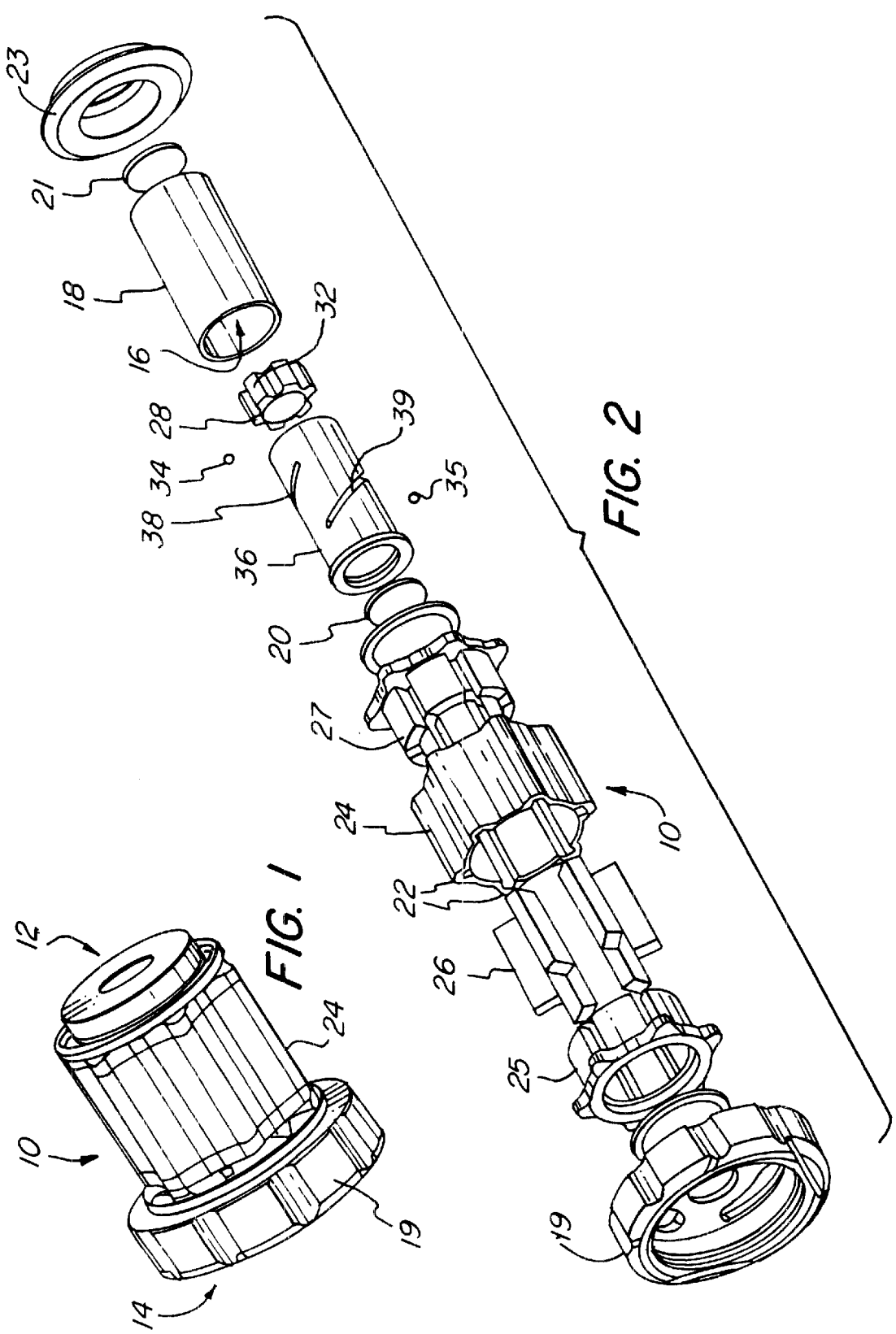

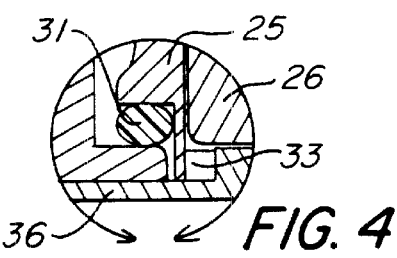
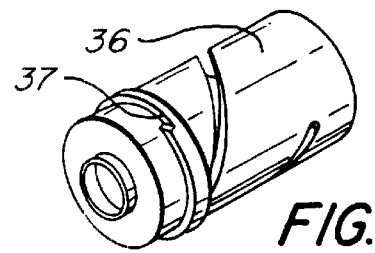
FIG. 4  FIG. 5
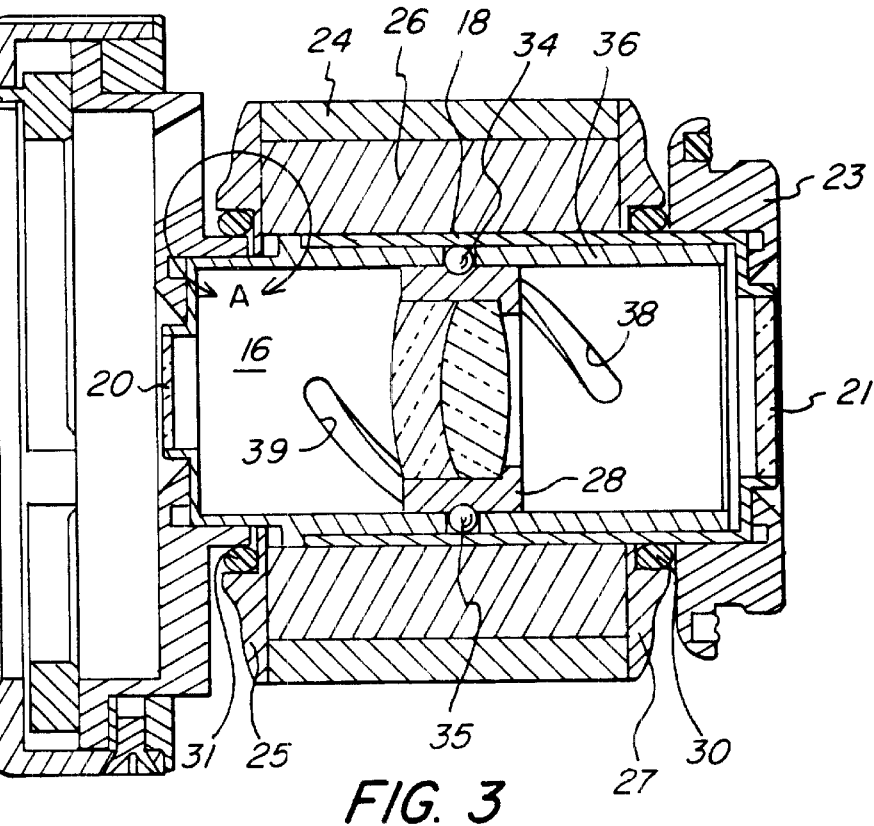
FIG. 3
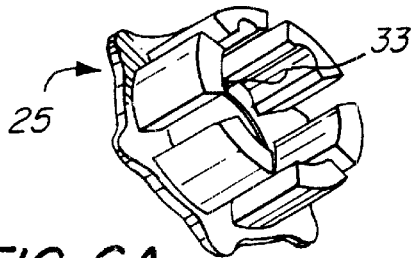
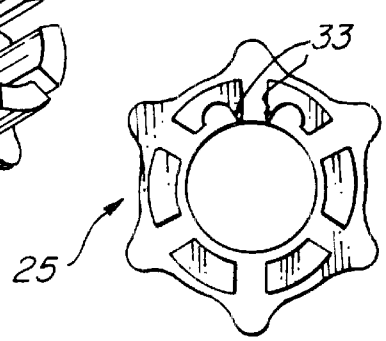
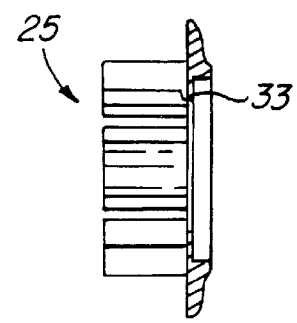
FIG. 6A  FIG. 6B  FIG. 6C

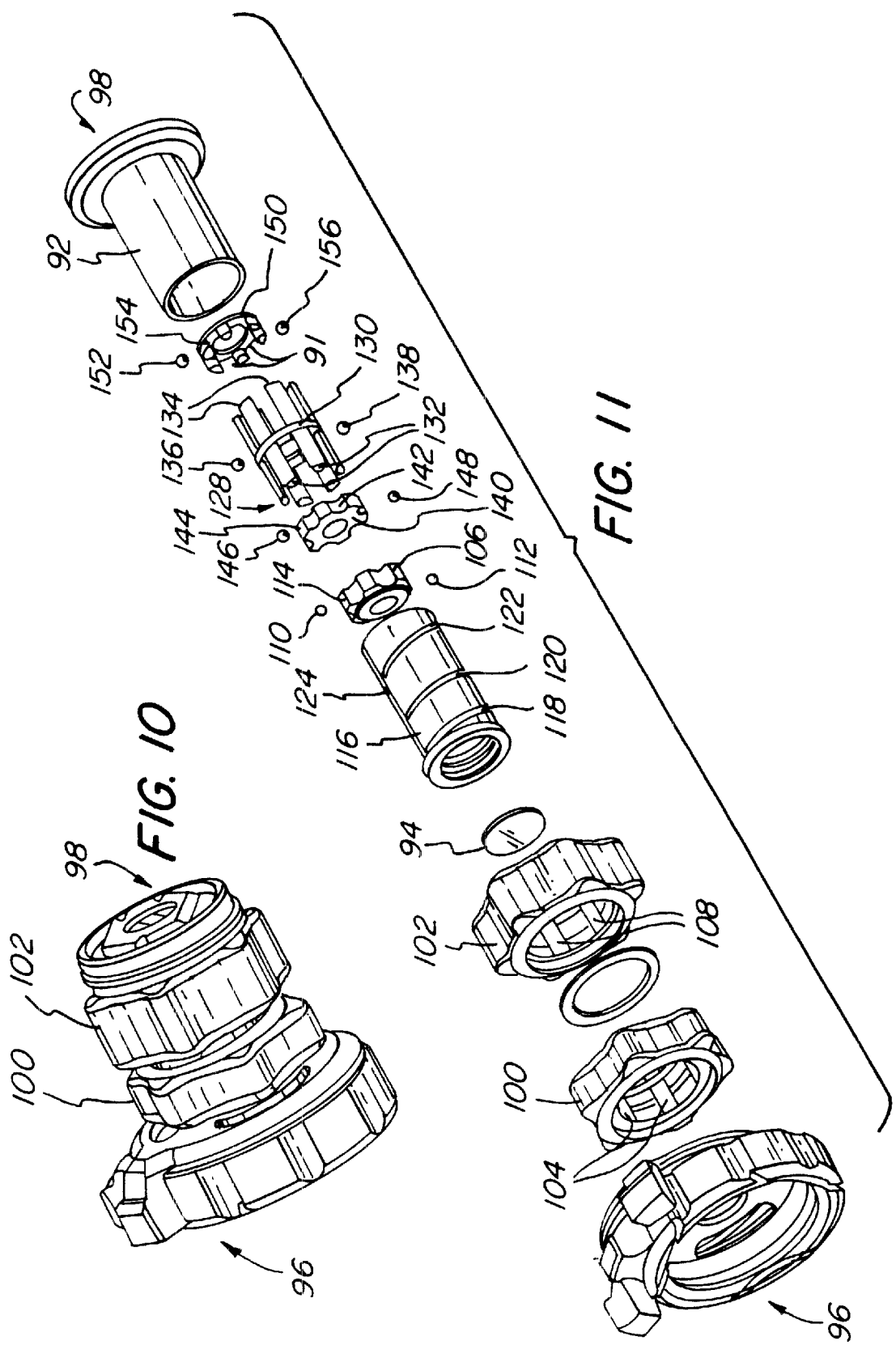

ENDOSCOPIC VIDEO CAMERA WITH MAGNETIC DRIVE FOCUSING

This is a continuation of U.S. patent application Ser. No. 09/836,629, Filed Apr. 17, 2001, now U.S. Pat. No. 6,522,477.

FIELD OF THE INVENTION

The invention relates to endoscopic video cameras having lens assemblies inside a chamber that are axially movable due to the movement of magnets outside of the chamber.

BACKGROUND OF THE INVENTION

Endoscopes and endoscopic video cameras are now widely used by physicians during surgery to view inside body cavities. Typically, the endoscopic video camera contains an optical focusing lens and a focusing device that can be adjusted to optimize images transmitted by the endoscope. After each use with a patient, the endoscope and endoscopic video camera must be cleaned and sterilized before they can be used again. Typically, sterilization is performed either by high temperature steam autoclaving or by submersion in a sterilizing liquid. Due to cost and time considerations, it is desirable to sterilize both endoscopes and endoscopic video cameras using high temperature steam autoclaving.

One problem with previous endoscopic video camera designs is that direct mechanical linkages used to adjust the position of the lens expose the focusing lens to sterilization fluid, steam or other contaminants. To address this problem endoscopic video cameras have been developed that use lens in hermetically sealed interior chambers and use magnetic drives to move the lens axially within the interior chamber for focusing purposes. Such endoscopic video cameras are described in U.S. Pat. No. 5,359,992 issued to Hori et al., and U.S. Pat. No. 5,056,902 issued to Chinnock et al. In these designs, internal magnets connected to the lens within the interior chamber move in response to the rotation of external magnets located around the periphery of the interior chamber. However, magnet only focusing may not permit sufficient focusing precision and may not have sufficient holding strength to maintain the lens in the optimum focusing position. Further, these prior art designs have mechanical linkages outside the interior chamber that, like the prior art designs, are exposed to sterilization fluid, steam and other contaminants. Additionally, because there is no direct mechanical linkage between the magnets outside the interior chamber and the magnets inside the interior chamber, a drop, sudden shaking or knocking of the device may result in a break down in the magnetic connection between the inner and outer structures and the magnetic connection between the internal and external magnets can be lost permanently.

In an effort to avoid these problems, other endoscopic video camera designs have moved the mechanical linkage inside the sealed chamber. Examples of such designs are U.S. Pat. No. 5,978,161 issued to Lemke ("Lemke"), U.S. Pat. No. 5,835,865 issued to Speier et al. ("Speier") and U.S. Pat. No. 5,706,143 issued to Hipp ("Hipp"). However, these designs require machining of lens cells with helical grooves and magnet seats, mechanical linkages to connect the internal magnets to the lens or they require the internal magnet to travel within a helical channel in order to convert the rotational movement of the internal magnets to linear movement of the lens. For example, in Lemke the holder that carries the lens must be machined or formed to have a helical guiding groove and seats for the internal magnet. In Speier, the internal magnets are fixed to a rotatable cylinder having a pin. The rotation of the internal magnets rotates the pin that is mechanically linked to a helical groove formed on the outside diameter of the lens forcing the lens to move axially. In another example, in Hipp, the separate internal magnet is attached to the lens and the magnet must travel within a helical channel formed in a sleeve as the lens rotates.

What is needed therefore is a magnetic focusing device with a simplified design having a sealed cylinder that makes the device easy to operate, eliminates complex mechanical linkages, reduces the amount of machining done to the lens, resists shocks due to dropping or shaking, and permits precision focusing.

SUMMARY OF THE INVENTION

Accordingly, it is an object of the invention to provide a device and method using magnetic forces to position and focus a lens within a sealed chamber that does not require a mechanical linkage between the lens and internal magnets.

Another object of the invention is to provide a device having a lens within a sealed chamber that does not require a mechanical linkage between an internal magnet and the lens to convert the rotational movement of the internal magnet to axial movement of the lens.

A further object of the invention is to provide a device having a magnetizable lens that rotates in response to rotation of an external magnetic adjuster.

Yet another object of the invention is to provide a device that does not require an internal magnet travel within a helical channel.

Yet a further object of the invention is to provide a device with a fixed intermediate sleeve having helical grooves that provide paths for guides to travel and guide the lens in a combination of rotational and axial movement, eliminating the need to machine guide grooves or magnet seats directly into the lens.

Still another object of the invention is to provide a device that uses a magnetic field to adjust lenses without requiring both internal and external magnets.

Still another object of the invention is to provide a device having a focusing lens and zoom lenses that can be adjusted independently using separate magnetic drives.

The invention and its particular features and advantages will become more apparent from the following detailed description considered with reference to the accompanying drawings.

BRIEF DESCRIPTION OF THE DRAWINGS

FIG. 1 is a perspective view of a first embodiment of the magnetic drive focusing device with a single adjuster.

FIG. 2 is an exploded view of the components in the first embodiment of the magnetic drive focusing device with a single adjuster.

FIG. 3 is a cross-sectional side view of the first embodiment shown in FIG. 1.

FIG. 4 is an enlargement of area A in FIG. 3.

FIG. 5 is a detailed perspective view of the fixed sleeve 36 shown in FIG. 3.

FIG. 6A depicts a perspective view of magnet spacer 25 shown in FIG. 3.

FIG. 6B depicts an end view of magnet spacer 25 shown in FIG. 3.

FIG. 6C depicts a cross-sectional side view of magnet spacer 25 shown in FIG. 3.

FIG. 10 is a perspective view of a third embodiment of the magnetic drive focusing device with two adjusters.

FIG. 11 is an exploded view of the components in the third embodiment shown in FIG. 10.

DETAILED DESCRIPTION OF THE DRAWINGS

Figure 7:
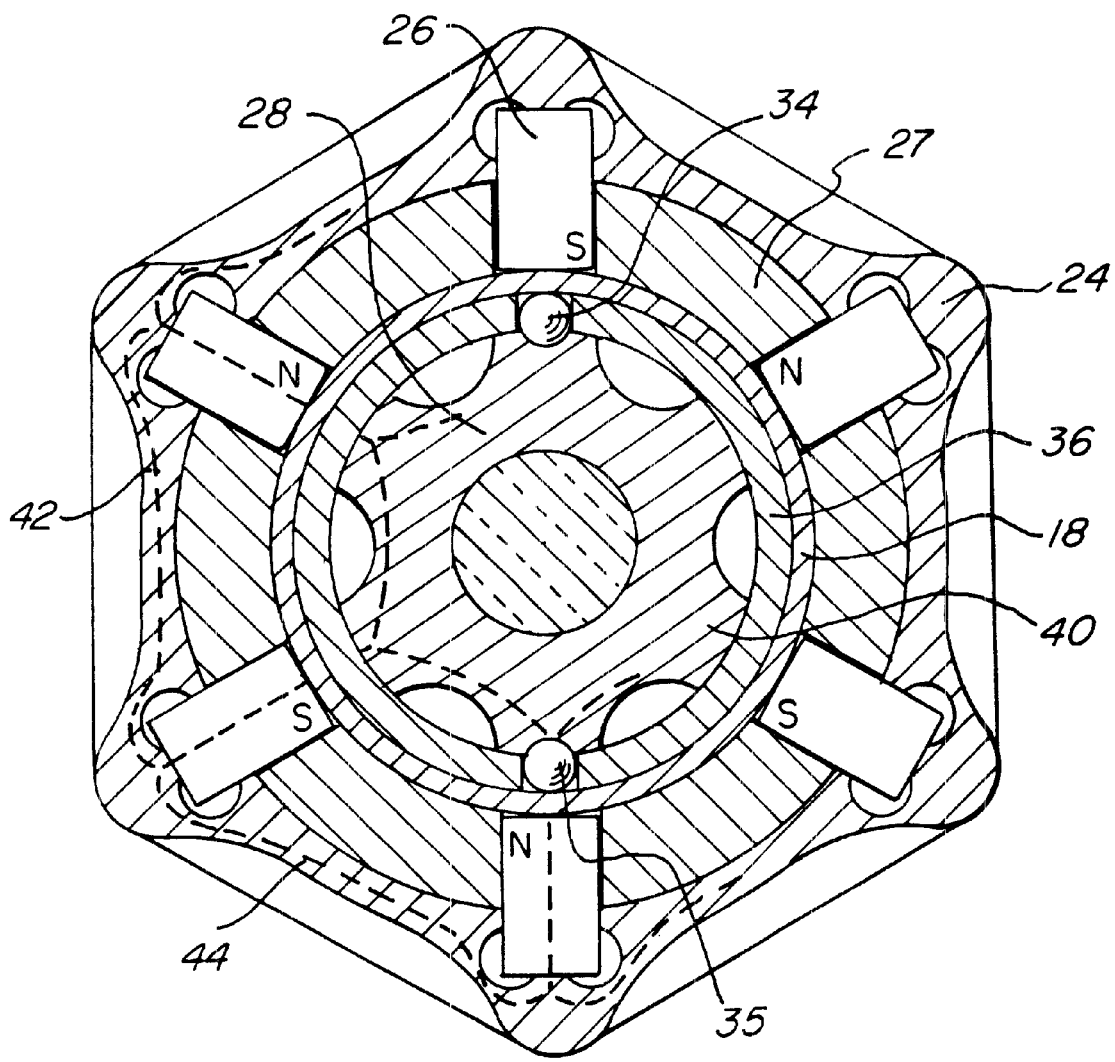
FIG. 7 is a cross-sectional end view of the first embodiment shown in FIG. 1.

FIG. 1 is a drawing of a first embodiment of the invention showing the magnetic drive focusing device 10 with a single external adjuster 24. The focusing device having a proximal end 14 and a distal end 12. FIG. 2 is a drawing of the exploded view of the magnetic drive focusing device 10. Device 10 includes an interior chamber 16. Interior chamber 16 is defined at least partially by a sleeve 18. The interior chamber can be further defined by two transparent windows 20, 21; with first window 20 being located nearest the proximal end of sleeve 18, where endoscope mount 19 is located, and second window 21 being located nearest the distal end of sleeve 18 where endoscopic video camera chassis mount 23 is located. Interior chamber 16 is preferably sealed or even more preferably hermetically sealed. Fixed cylinder 36 and sleeve 18 can be closed or sealed by first and second windows 20, 21 or sleeve 18, on its distal end, can be closed or sealed by other means such as being welded or sealing attached to the endoscopic video camera chassis or by attaching a sealing cap to the distal end. Fixed sleeve 36 and sleeve 18 are made of non-magnetic material, such as ceramic, titanium, plastic, or non-magnetic stainless steel.

Around interior chamber 16 is external adjuster 24, preferably made of magnetic stainless steel, that is moveable around the periphery of interior chamber 16. Adjuster 24 carries magnetizable portion around the periphery of interior chamber 16 as adjuster 24 is moved. In the embodiment shown in FIG. 2, adjuster 24 carries six separate external magnets 26. External magnets 26 are positioned in place axially and radially by grooves 22 in the inside diameter of adjuster 24 and by magnet spacers 25, 27. Magnet spacers 25, 27 are preferably made of non-magnetic material or non-magnetic metal.

Inside interior chamber 16 is a lens 28. Lens 28 includes at least a portion transparent to visible light and a magnetizable portion responsive to magnetic fields. Preferably, the magnetizable portion of lens 28 is made of magnetic stainless steel. Lens 28 could also be made of a non-magnetic material with magnetic inserts that would respond to the magnetic fields created by external magnets 26. Connected with the exterior of lens 28 are two non-magnetic guides 34 and 35 positioned on it in a fixed position relative to lens 28. In the first embodiment guides 34 and 35 are non-magnetic balls, that sit in dimple 32 on the exterior of lens 28. Dimple 32 forms the seat for the non-magnetic guide 34. A second dimple, not shown in FIG. 2, on the exterior of lens 28 acts as a seat for non-magnetic guide 35 (refer to FIG. 7.) Various other types of non-magnetic guides of plastic, ceramic or non-magnetic metals could also be employed including various arrangements such as a pin mounted or fixed to the exterior of lens 28. Preferably, the non-magnetic guides are polytetraflouroethylene (PTFE) balls.

Fixed sleeve 36 has two helical grooves 38, 39 cut through its periphery. When the magnetic drive focusing device is assembled, non-magnetic guides 34, 35 are positioned to sit both in the dimple seats on lens 28 and in the helical grooves 38, 39 of fixed sleeve 36.

The first embodiment of the invention operates in the following manner (refer to FIG. 7). External magnets 26, preferably being made of a SmCo composition, create six separate magnetic paths (two being depicted by lines 42 and 44). The six magnetic paths are produced by having each separate magnet 26 oriented so that the polarity of each alternates closest to sleeve 18. The magnetizable portion of lens 28 is fashioned in such a way as to have protrusions 40 which correspond in placement to each magnet 26. Adjuster 24, and protrusions 40 of the magnetizable portion of lens 28, both being preferably made of magnetic stainless steel, provide a magnetic path for the six magnetic paths (such as the two depicted by dashed lines 42 and 44). The magnetic fields created by magnets 26 need only be sufficient to move lens 28 within interior chamber 16. In this embodiment, to preclude the creation of magnetic paths which would prevent or degrade the magnetic fields from passing through the magnetizable portions of lens 28; magnet spacers 25,27, sleeve 18, fixed sleeve 36, and guides 34, 35 are composed of non-magnetic material, such as ceramic, titanium, plastic, or non-magnetic metal. More or fewer magnets, and different shaped magnets, can be used depending on the strength of the magnetic field they create, and the magnetic path created, to sufficiently move lens 28 within interior chamber 16.

It is understandable to those of ordinary skill in the art that magnetic fields sufficient to cause a magnetic connection between the adjuster and lens can similarly be created by reversing the position of magnets 26 outside sleeve 18 with the protrusions 40 of lens 50 inside sleeve 18.

When optimization (focusing) of the endoscopic image is required, lens 28 is repositioned within interior chamber 16. As external magnets 26 are rotated about interior chamber 16 by rotation of adjuster 24, the magnetic field connection between adjuster 24 and the magnetic responsive portion of lens 28 forces lens 28 to rotate. As lens 28 rotates, the non-magnetic guides 34, 35 seated in dimples on lens 28 are forced along helical grooves 38, 39 of fixed sleeve 36. As non-magnetic guides 34, 35 move along helical grooves 38, 39 they in turn force lens 28 to translate in an axial direction within interior chamber 16. As lens 28 translates axially, non-magnetic guides 34, 35 also move axially, maintaining their axial position relative to lens 28. Reversing the direction of rotation of adjuster 24 reverses the axial direction of movement of lens 28. Thus, the operator can adjust the position of lens 28 to optimize the focus of the visual image generated by the endoscope by rotating adjuster 24.

As previously described, adjuster 24 moves freely about sleeve 18. Without friction or tension being provided against adjuster 24, the desired focus setting (lens position) would be inadvertently lost due to further handling and movement of the device. Friction against adjuster 24 is provided by a tensioner preferably pliable o-rings 30 and 31 (FIG. 3). Pliable o-rings 30 and 31 have a sufficient diameter that allows for deformation of the o-ring, which in turn provides adequate tension to hold the adjuster in place between adjustments while also allowing ease of rotation of adjuster 24 by hand. Moreover, pliable o-rings 30 and 31 hold adjuster 24 parallel to sleeve 18 during rotation of adjuster 24. Various other materials and tension producing methods could be used to provide the desired balance between tension and ease of rotation of adjuster 24; such materials and methods include, but are not limited to, metal bushings, pins and grooves, and ball bearings and raceways, and the like.

As adjuster 24 is rotated causing lens 28 to also rotate, guides 34, 35 are forced along their corresponding helical grooves 38, 39 (refer to FIGS. 3 and 7). Once the limits of the helical grooves are reached (in both rotational directions), the rotation and axial displacement of lens 28 halts. If adjuster 24 continues to be rotated once the limits of helical grooves 38, 39 are reached by guides 34, 35; magnets 26 will continue past the now fixed protrusions 40 of lens 28. As magnets 26 overpass protrusions 40, the corresponding magnetic field is lost, and an unwanted and reverse rotation of lens 28 occurs. In the preferred embodiment, as depicted in FIGS. 5 and 6A, to prevent this reverse rotation of lens 28, the device has a stop, preferably the fixed sleeve 36 has a stop groove 37 in its periphery, in which magnet spacer 25 stop tabs 33 rests (refer to detail FIG. 3). Stop groove 37 is aligned in such a manner as to correspond to the limits of helical grooves 38, 39 of fixed sleeve 36. As lens 28 reaches the limits of rotation caused by helical grooves 38, 39; stop tabs 33 reach the limits of stop groove 37; preventing rotation of adjuster 24 and magnets 26, held in adjuster 24, from over passing protrusions 40 of lens 28. Various other arrangements of stops and stops with tabs and grooves could be employed to prevent the continuous rotation of adjuster 24 and prevent an unwanted and reverse rotation of lens 28.

Figure 8:
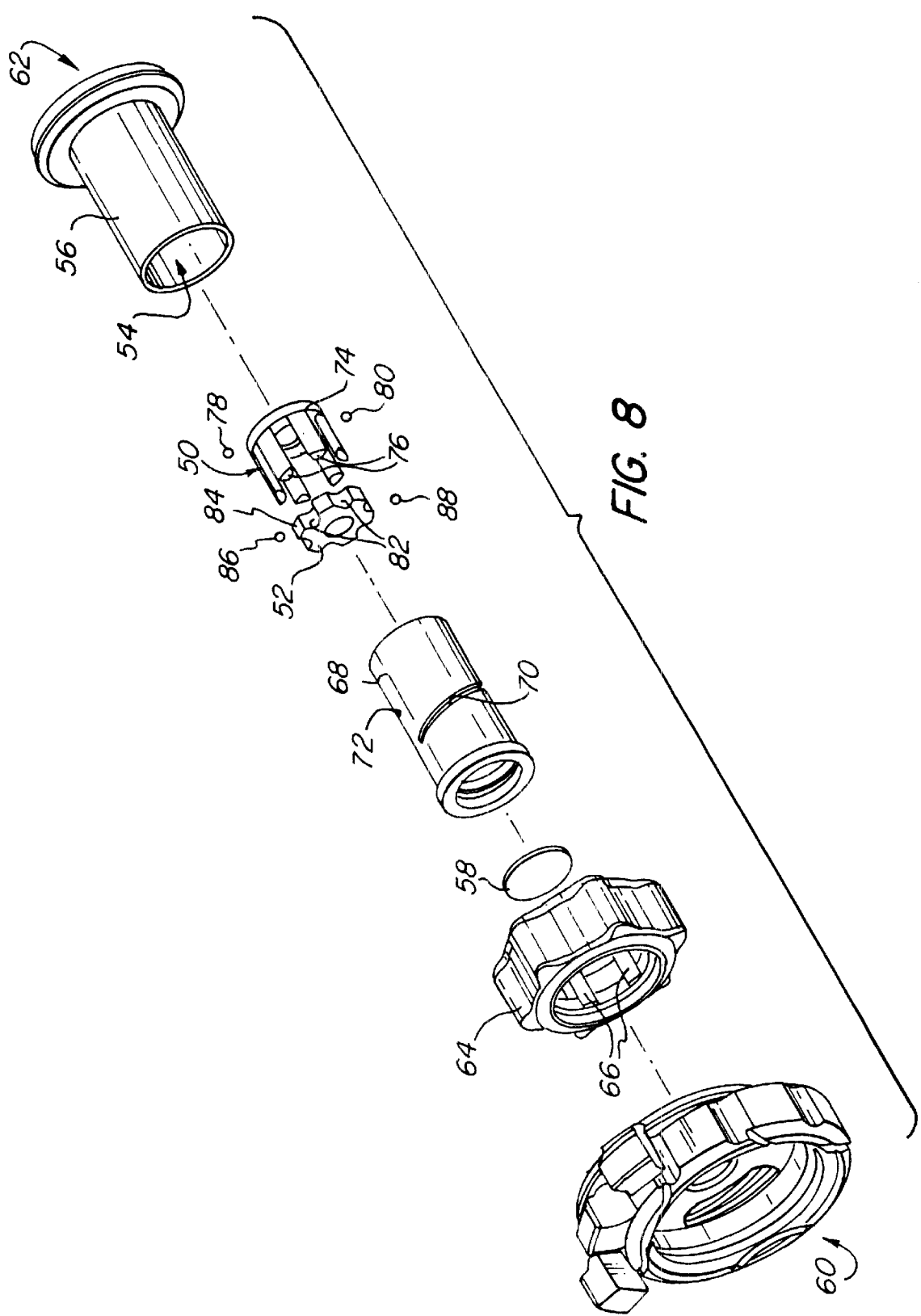
FIG. 8 is an exploded view of a second embodiment of the magnetic drive focusing device with two lenses.
Figure 9:
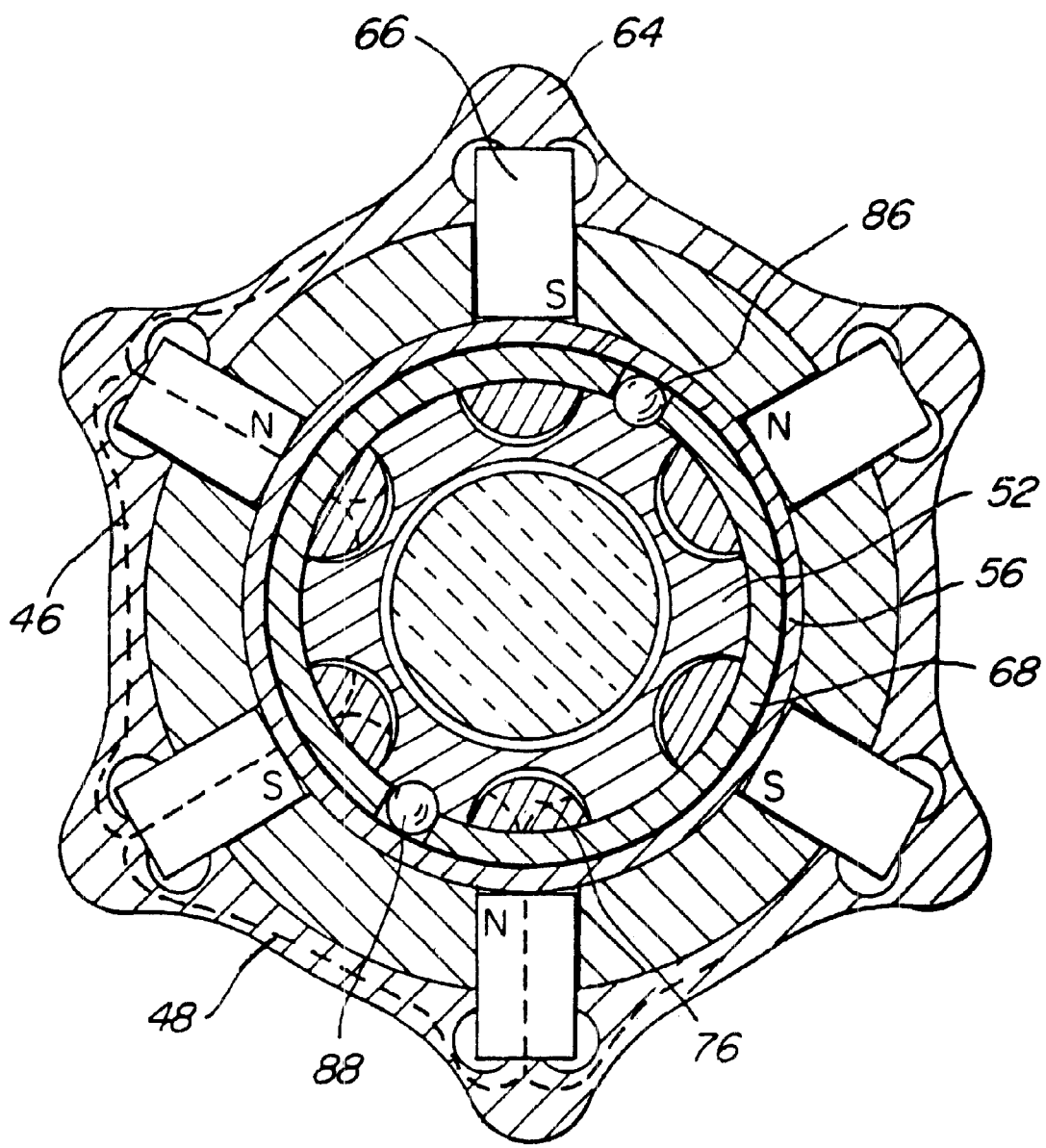
FIG. 9 is a cross-sectional view of the second embodiment shown in FIG. 8.

In a second embodiment, FIGS. 8 and 9 depict a two lens focusing system with a first magnetic lens 50 and a second non-magnetic lens 52. First lens 50 includes at least a portion transparent to visible light, and a magnetizable portion responsive to magnetic fields, such as a magnetic metal. Preferably, the portion of first lens 50 that is responsive to magnetic fields is made of magnetic stainless steel. Magnetic first lens 50 could also be made of non-magnetic material with magnetic inserts or magnets that would respond to the magnetic fields created by external magnets 66. Non-magnetic second lens 52 includes at least a portion transparent to visible light, and a portion non-responsive to magnetic fields, such as non-magnetic material. Preferably, the portion of second lens 52 not responsive to magnetic fields is made of non-magnetic stainless steel. The second embodiment includes an interior chamber 54 that is at least partially defined by an outer sleeve 56. The interior chamber can be further defined by a transparent window 58. Interior chamber 54 is preferably sealed or even more preferably hermetically sealed. Outer sleeve 56 can be closed or sealed by window 58 on its proximal end 60, and it can be closed or sealed on its distal end 62 by other means such as being welded or sealing attached to the endoscopic video camera chassis or by attaching a sealing cap to the distal end. Outer sleeve 56 is preferably made of non-magnetic stainless steel.

Around interior chamber 54 is an adjuster 64. Adjuster 64 is preferably made of magnetic stainless steel and carries a magnetizable portion 66 around the periphery of outer sleeve 56 as adjuster 64 is rotated. In the embodiment shown in FIGS. 8 and 9, adjuster 64 carries six separate external magnets 66. External magnets 66 are positioned in place laterally and axially in the inside diameter of adjuster 64, and create magnetic fields within interior chamber 54 that are capable of acting upon the magnetizable portion of lens 50 positioned within interior chamber 54. External magnets 66, are preferably made of a SmCo composition. The magnetic field created by the magnetic material need only be sufficient to move lens 50 within the interior chamber 54. More or less magnets, different magnetic material and different shaped magnets can be used, depending on the strength of the magnetic field they create, and the magnetic path created, to sufficiently move lens 50 within interior chamber 54.

Located inside interior chamber 54 is a fixed cylinder or sleeve 68. Fixed sleeve 68 is made of non-magnetic material. Fixed sleeve 68 is held in a fixed position relative to outer sleeve 56. Fixed sleeve 68 has two helical grooves and two apertures cut through its periphery. First helical groove 70 and aperture 72 are shown only in FIG. 8. Magnetic first lens 50 is positioned inside fixed sleeve 68, and has a raceway 74 around its periphery and preferably a set of protrusions or fingers 76 which extend proximally from raceway 74. Magnetic first lens 50 is oriented within fixed cylinder 68 to permit a first non-magnetic guide ball 78 to be positioned both on raceway 74 and in aperture 72 of fixed cylinder 68. In the preferred embodiment, a second non-magnetic guide ball 80 is also positioned both on raceway 74 and in another aperture (not shown) in fixed sleeve 68. Preferably, non-magnetic guides 78 and 80 are polytetraflouroethylene (PTFE) balls.

Non-magnetic second lens 52 is positioned within interior chamber 54 proximal to magnetic first lens 50. Non-magnetic second lens 52 has recesses 82 around its periphery that allow the fingers 76 of magnetic first lens 50 to engage the recesses 82 of non-magnetic second lens 52. Other connectors or mechanical linkages could also be used, providing they transfer the rotational movement of magnetic first lens 50 to rotational movement of non-magnetic second lens 52. Non-magnetic second lens 52 also has dimple seats (only dimple 84 is shown in FIG. 8) on its exterior, similar to lens 28 in the first embodiment. When the present embodiment of the magnetic drive focusing device is assembled, non-magnetic second lens 52 is oriented so that a third non-magnetic guide 86 is positioned to sit both on dimple seat 84 and in helical groove 70 of fixed cylinder 68. In the preferred embodiment, a fourth non-magnetic guide 88 is also positioned to sit both on a second dimple seat (not shown) on non-magnetic second lens 52 and in a different helical groove (not shown) within the periphery of fixed cylinder 68.

In the present embodiment, when the invention is in operation, external magnets 66 create six separate magnetic paths (two being depicted by dashed lines 46 and 48 of FIG. 9). The six magnetic paths are produced by having each separate magnet 66 oriented so that the polarity of each alternates closest to sleeve 56. The magnetizable portion of lens 50 is fashioned in such a way as to have protrusions 76 which correspond in placement to each magnet 66. Accordingly, when adjuster 64 is rotated, magnetic first lens 50 also moves. However, unlike lens 28 in the first embodiment, when magnetic first lens 50 is moved, it does not translate axially within the device. Instead, magnetic first lens 50 maintains its relatively fixed axial position within interior chamber 54. Magnetic first lens 50 maintains its relatively fixed axial position because as it rotates, the first non-magnetic guide 78 remains in its respective aperture 72 while maintaining contact with the rotating raceway 74 of magnetic first lens 50, thus preventing raceway 74 of magnetic first lens 50 from moving axially. Non-magnetic guide 78 maintains its axial position relative to magnetic first lens 50. The third and fourth non-magnetic guides 86, 88 are preferably PTFE balls, however other types of guides such as pins or cylinders could also be used. Alternatively, snap rings, shoulders, pins or some other types of stops could also be placed in the insider diameter of the sealed cylinder 56 to prevent axial movement of magnetic first lens 50 within interior chamber 54.

It is understandable to those of ordinary skill in the art that magnetic fields sufficient to cause a magnetic connection between the adjuster and lens can similarly be created by reversing the position of magnets 66 outside sleeve 56 with the protrusions 76 of lens 50 inside sleeve 56.

In operation, as magnetic first lens 50 rotates, proximally extending fingers 76 that engage the recesses 82 of non-magnetic second lens 52 cause non-magnetic second lens 52 to rotate. As non-magnetic second lens 52 rotates, the third non-magnetic guide 86 sitting in dimple seat 84 on non-magnetic second lens 52 is forced along helical groove 70. Fourth non-magnetic guide 88 is also forced along a separate helical groove (not shown). As third and fourth non-magnetic guides 86, 88 travel along their respective helical grooves, they in turn force non-magnetic second lens 52 to translate in an axial direction within interior chamber 54. As non-magnetic second lens 52 translates axially, non-magnetic guides 86, 88 also move axially, maintaining their axial position relative to non-magnetic second lens 52.

As previously described in the first embodiment, without friction or tension being provided against adjuster 64, the desired focus setting (lens position) of the device would be inadvertently lost due to further handling and movement of the device. Friction or tension against the adjuster 64 is provided by a tensioner, preferably pliable o-rings, similar to o-rings 30 and 31 in FIG. 3. The pliable o-rings have a sufficient diameter, that allows for deformation of the o-ring, which in turn provides adequate tension to hold the adjuster in place between adjustments while also allowing ease of rotation by hand. Moreover, the pliable o-rings hold the adjuster parallel to sleeve during rotation of the adjuster. Various other materials and tension producing methods could be used to provide the desired balance between tension and ease of rotation of the adjuster. Such materials and methods that could be used are, but not limited to, metal bushings, pins and grooves, and ball bearings and raceways, and the like.

Continuous rotation of adjuster 64 and consequent unwanted lens rotation can be prevented by stops in the present embodiment using stops similar to those described in the first embodiment.

The invention is not limited to the preferred embodiment with a first lens with fingers that extend proximally as connectors, but also would include embodiments with a first lens having fingers or connectors that extend distally. Other embodiments of the invention also include a first lens with one or more fingers or other arrangements, linkages or connectors that would permit the rotating first lens to rotate the second lens. For example, the invention would also cover the use of cylinders or rods extending from the first lens through holes in the second lens or similar arrangements.

A third embodiment of the invention is a multi-lens focus and zoom device having four movable lenses, as shown in FIG. 10. FIG. 11 shows the components that make up the multi-lens focus and zoom device in FIG. 10. The third embodiment includes an interior chamber 90 that is at least partially defined by an outer sleeve 92. Outer sleeve 92 is preferably made of non-magnetic stainless steel. Interior chamber 90 can be further defined using transparent window 94. Interior chamber 90 is preferably closed or more preferably sealed and even more preferably hermetically sealed. First window 94, closes or seals fixed cylinder or sleeve 116, which in turn closes or seals interior chamber 90 at its proximal end 96. Outer sleeve 92 is made of a non-magnetic material, and can be closed or sealed at its distal end 98 by a second window (not shown), or by other means such as being welded or sealing attached to the endoscopic video camera chassis or by attaching a sealing cap.

Around interior chamber 90 are a first adjuster 100 and a second adjuster 102, that are independently moveable around the periphery of interior chamber 90.

Adjuster ring 100, preferably made of magnetic stainless steel, carries magnetizable material 104 around the periphery of interior chamber 90 as adjuster 100 is rotated. In the embodiment shown in FIG. 11, external adjuster 100 carries six separate external magnets 104. External magnets 104 are positioned in place axially and radially by grooves in the inside diameter of external adjuster 100 and by magnet spacers. The magnet spacers are preferably made of non-magnetic material or non-magnetic metal.

Inside interior chamber 90 is a lens 106. Lens 106 includes at least a portion transparent to visible light and a magnetizable portion responsive to magnetic fields, such as a magnetic material. Preferably the magnetizable portion of lens 106 is made of magnetic stainless steel. Lens 106 could also be made of a non-magnetic metal with magnetic inserts that would respond to the magnetic fields created by external magnets 104. Connected with the exterior of lens 106 are two non-magnetic guides 110 and 112 positioned on it in a fixed position relative to lens 106. In the present embodiment, guides 110 and 112 are non-magnetic balls that rest in dimple seats (only dimple seat 114 is shown in FIG. 11) on the exterior of lens 106. Dimple 114 forms the seat for the non-magnetic guide 110. A second dimple, not shown in FIG. 11, on the exterior of lens 106 acts as a seat for non-magnetic guide 112. Various other types of non-magnetic guides of plastic, ceramic or non-magnetic metals could also be employed including various arrangements such as a pin mounted or fixed to the exterior of lens 106. Preferably, the non-magnetic guides are polytetraflouroethylene (PTFE) balls.

Fixed sleeve 116, is made of non-magnetic material and is held in a fixed position relative to sleeve 92. Fixed sleeve 116 has six helical grooves cut through its periphery (helical grooves 118, 120, and 122 are shown in FIG. 11). When the magnetic drive focusing device is assembled, non-magnetic guides 110, 112 are positioned to sit both in the dimple seats on lens 106 and in helical grooves 118, of fixed sleeve 36 (the helical groove corresponding to non-magnetic guide 112 is not shown in FIG. 11).

As described in the first embodiment of the invention, the present embodiment operates in the following manner (refer to FIG. 12). External magnets 104, preferably being made of a SmCo composition, create six separate magnetic paths (two being depicted by dashed lines 107 and 109). The six magnetic paths are produced by having each separate magnet 104 oriented so that the polarity of each alternates closest to sleeve 92. The magnetizable portion of lens 106 is fashioned in such a way as to have protrusions 111 which correspond in placement to each magnet 104. Adjuster 100, and protrusions 111 of the magnetizable portion of lens 106, both being preferably made of magnetic stainless steel, provide a magnetic path for the six magnetic paths (such as the two depicted by dashed lines 107 and 109). The magnetic fields created by magnets 104 need only be sufficient to move lens 106 within interior chamber 90. In this embodiment, to preclude the creation of magnetic paths which would prevent or degrade the magnetic fields from passing through the magnetizable portions of lens 106; magnet spacers, sleeve 92, fixed sleeve 116, and guides 110, 112 are composed of non-magnetic material or non-magnetic metal. More or fewer magnets, and different shaped magnets, can be used depending on the strength of the magnetic field they create, and the magnetic path created, to sufficiently move lens 106 within interior chamber 90.

As with the first embodiment, it is understandable to those of ordinary skill in the art that magnetic fields sufficient to cause a magnetic connection between the adjuster and lens can similarly be created by reversing the position of magnets 104 outside sleeve 92 with protrusions 111 inside sleeve 92.

When optimization (focusing) of the endoscopic image is required, lens 106 is repositioned within interior chamber 90. As external magnets 104 are rotated about interior chamber 90 by rotation of adjuster 100, the magnetic field connection between adjuster 100 and the magnetizable portion of lens 106 forces lens 106 to rotate. As lens 106 rotates, non-magnetic guides 110, 112 sitting in dimples on lens 106 are forced along the helical grooves (only groove 118 is shown in FIG. 11) of fixed sleeve 116. As non-magnetic guides 110, 112 move along the helical grooves, they in turn force lens 106 to translate in an axial direction within interior chamber 90. As lens 106 translates axially, non-magnetic guides 110, 112 also move axially, maintaining their axial position relative to lens 106. Reversing the direction of rotation of adjuster 100 reverses the axial direction of movement of lens 106. Thus, the operator can adjust the position of lens 106 to optimize the focus of the visual image generated by the endoscope by moving adjuster 100.

Also around interior chamber 90 is a second adjuster 102, preferably made of magnetic stainless steel that is moveable around the periphery of interior chamber 90. Adjuster 102 carries a magnetizable portion 108 around the periphery of interior chamber 90 as adjuster 102 is rotated. In the embodiment shown in FIG. 11, external adjuster 102 carries six separate external magnets 108. External magnets 108 are positioned in place axially and radially by grooves in the inside diameter of external adjuster 102 and by magnet spacers. The magnet spacers are preferably made of non-magnetic material or non-magnetic metal.

In the embodiment shown in FIG. 11, second lens 128 includes at least a portion transparent to visible light, and a magnetizable portion responsive to magnetic fields, such as magnetic material. Preferably, the portion of second lens 128 that is responsive to magnetic fields is made of magnetic stainless steel. Magnetic second lens 128 could also be made of non-magnetic material with magnetic inserts that would respond to the magnetic fields created by external magnets 108. Third lens 140 includes at least a portion transparent to visible light, and a portion non-responsive to magnetic fields, such as non-magnetic material. Preferably, the portion of third lens 140 not responsive to magnetic fields is made of non-magnetic stainless steel.

Magnets 108, held inside second adjuster 102, create magnetic fields within interior chamber 90 that are capable of acting upon magnetic second lens 128 positioned within interior chamber 90. External magnets 108, are preferably made of a SmCo composition. The magnetic field created by the magnetic material need only be sufficient to move ferromagnetic second lens 128 within the interior chamber 90. More or less magnets, different magnetic material and different shaped magnets can be used, depending on the strength of the magnetic field they create, and the magnetic path created, to sufficiently rotate magnetic second lens 128 within interior chamber 90.

Magnetic second lens 128 is positioned inside fixed sleeve 116, and has a raceway 130 around its periphery and preferably two sets of protrusions or fingers. The first set of protrusions or fingers 132 extend proximally from raceway 130. The second set of protrusions or fingers 134 extend distally from raceway 130. Magnetic second lens 128 is oriented within fixed cylinder 116 to permit a third non-magnetic guide 136 to be positioned both on raceway 130 and in aperture 124 of fixed cylinder 116. In the preferred embodiment, a fourth non-magnetic guide 138 is also positioned both on raceway 130 and in another aperture (not shown) in fixed sleeve 116. Preferably, non-magnetic guides 136 and 138 are polytetraflouroethylene (PTFE) balls.

Non-magnetic third lens 140 is positioned within interior chamber 90 proximal to magnetic second lens 128. Non-magnetic third lens 140 has recesses 142 around its periphery that allow the proximally extending fingers 132 of magnetic second lens 128 to engage the recesses 142 of non-magnetic third lens 140. Other connectors or mechanical linkages could also be used, providing they transfer the rotational movement of magnetic second lens 128 to rotational movement of non-magnetic third lens 140. Non-magnetic third lens 140 also has dimple seats (only dimple seat 144 is shown in FIG. 11) on its exterior, similar to lens 52 in the second embodiment. When the multi-lens magnetic drive focus and zoom device is assembled, non-magnetic third lens 140 is oriented so that a fifth non-magnetic guide 146 is positioned to sit both on dimple seat 144 and in second helical groove 120 of fixed cylinder 116. In the preferred embodiment, a sixth non-magnetic guide 148 is also positioned to sit both on a second dimple seat (not shown) on non-magnetic third lens 140 and in a different helical groove (not shown) within the periphery of fixed cylinder 116.

Non-magnetic fourth lens 150 is also positioned within interior chamber 90 distal to magnetic second lens 128. Non-magnetic fourth lens 150 has recesses 91 around its periphery that allow the distally extending fingers 134 of magnetic second lens 128 to engage the recesses 91 of non-magnetic fourth lens 150. Other connectors or mechanical linkages could also be used, providing they transfer the rotational movement of magnetic second lens 128 to rotational movement of non-magnetic fourth lens 150. Non-magnetic fourth lens 150 also has dimple seats (only dimple seat 154 is shown in FIG. 11) on its exterior, similar to lens 52 in the second embodiment. When the multi-lens magnetic drive focus and zoom device is assembled, non-magnetic fourth lens 150 is oriented so that a seventh non-magnetic guide 152 is positioned to sit both on dimple seat 154 and in third helical groove 122 of fixed cylinder 116. In the preferred embodiment, a eighth non-magnetic guide 156 is also positioned to sit both on a second dimple seat (not shown) on non-magnetic fourth lens 150 and in a different helical groove (not shown) within the periphery of fixed cylinder 116.

Figure 13:
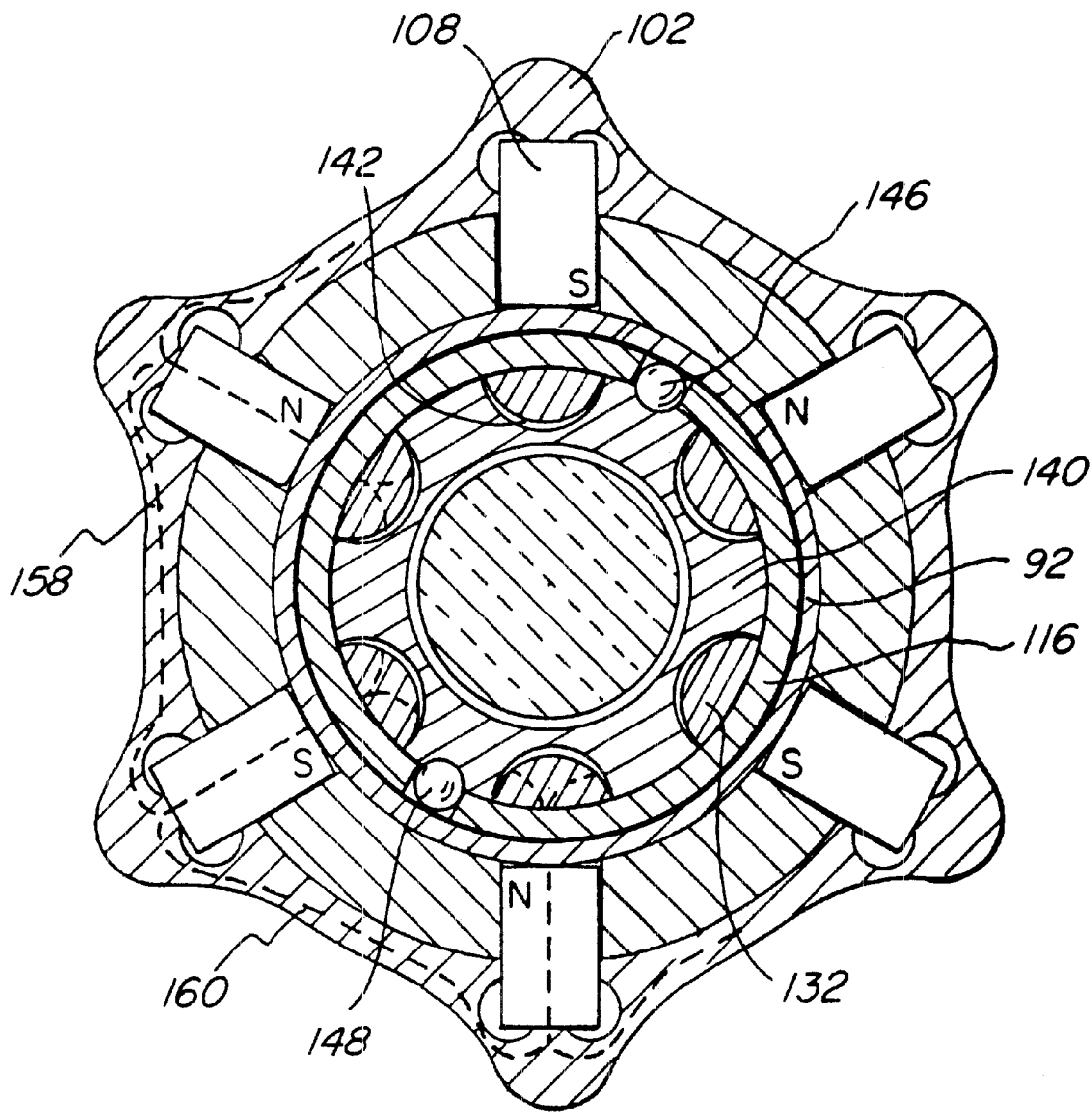
FIG. 13 is an additional cross-sectional end view of the third embodiment shown in FIG. 10.
Figure 14:
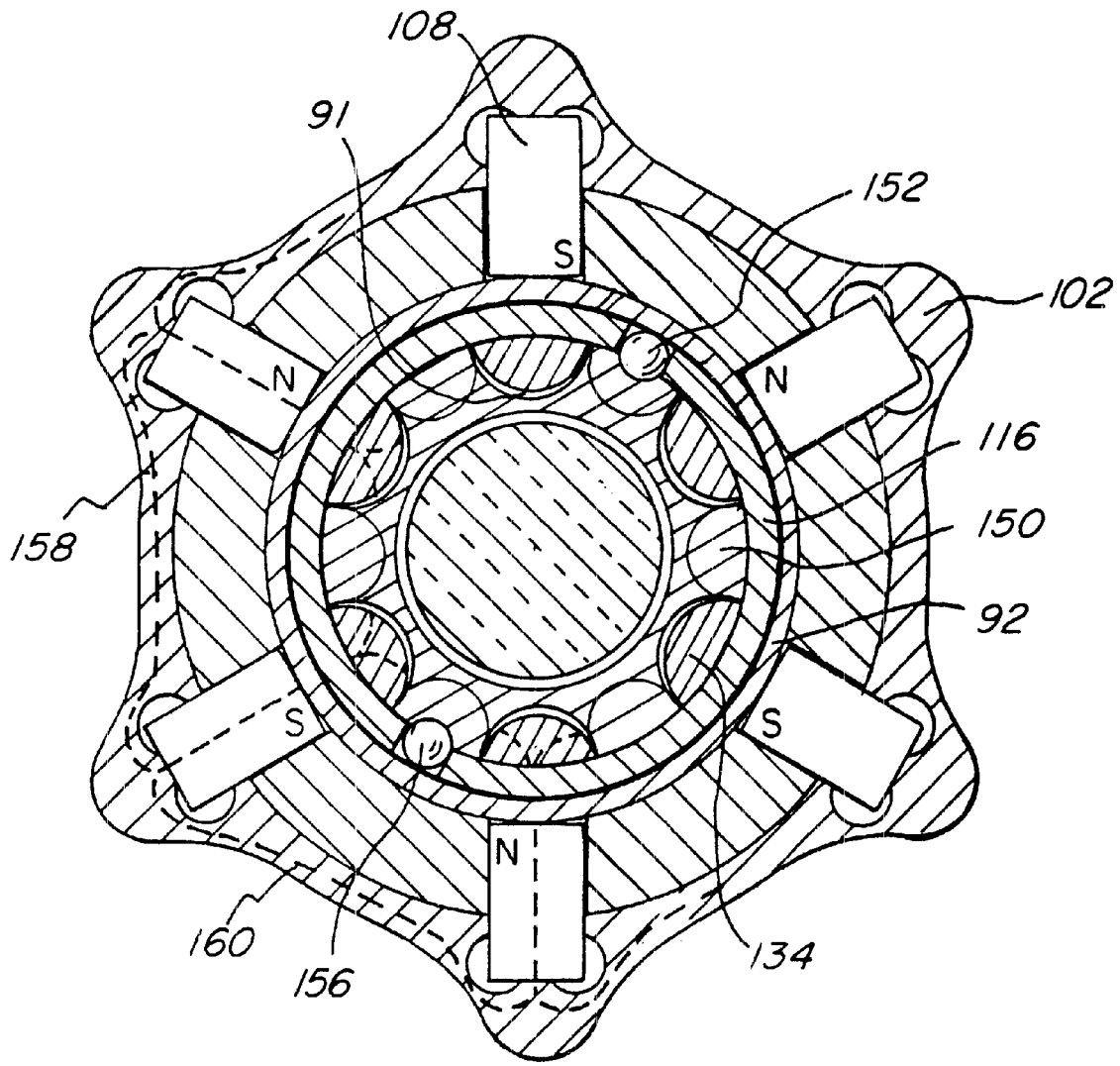
FIG. 14 is yet another cross-sectional end view of the third embodiment shown in FIG. 10.

In the present embodiment, when the invention is in operation, external magnets 108 create six separate magnetic paths (two being depicted by dashed lines 158 and 160 of FIGS. 13 and 14). Accordingly, when second external adjuster 102 is rotated, magnetic second lens 128 also rotates. However, unlike lens 28 in the first embodiment, when magnetic second lens 128 is rotated, it does not translate axially within the device. Instead, magnetic second lens 128 maintains its relatively fixed axial position within interior chamber 90. Magnetic second lens 128 maintains its relatively fixed axial position because as it rotates, non-magnetic guide 136 remains in its respective aperture 124 while maintaining contact with the rotating raceway 130 of magnetic second lens 128, thus preventing raceway 130 of magnetic second lens 128 from moving axially. Non-magnetic guide 138 maintains its axial position relative to magnetic second lens 128. Non-magnetic guides 136, 138 are preferably PTFE balls, however other types of non-magnetic guides such as pins or cylinders of ceramic or other non-magnetic materials could also be used. Alternatively, snap rings, shoulders, pins or some other types of stops could also be placed in the insider diameter of sealed cylinder 92 to prevent axial movement of magnetic second lens 128 within interior chamber 90.

As with the second embodiment, it is understandable to those of ordinary skill in the art that magnetic fields sufficient to cause a magnetic connection between the adjuster and lens can similarly be created by reversing the position of magnets 108 outside sleeve 92 with protrusions 132, 134 of lens. 128.

In operation, as magnetic second Lens 128 rotates, proximally extending fingers 132 that engage the recesses 142 of non-magnetic third lens 140 cause non-magnetic third lens 140 to rotate. As non-magnetic third lens 140 rotates, non-magnetic guide 146 sitting in dimple seat 144 on non-magnetic third lens 140 is forced along helical groove 120. Non-magnetic guide 148 is also forced along a separate helical groove (not shown). As non-magnetic guides 146, 148 travel along their respective helical grooves, they in turn force non-magnetic third lens 140 to translate in an axial direction within interior chamber 90. As non-magnetic third lens 140 translates axially, non-magnetic guides 146, 148 also move axially, maintaining their axial position relative to non-magnetic third lens 140.

Also in operation, as magnetic second lens 128 rotates, distally extending fingers 134 that engage the recesses 91 of non-magnetic fourth lens 150 cause non-magnetic fourth lens 150 to also rotate. As non-magnetic fourth lens 150 rotates, non-magnetic guide 152 sitting in dimple seat 154 on non-magnetic fourth lens 150 is forced along helical groove 122. Non-magnetic guide 156 is also forced along a separate helical groove (not shown). As non-magnetic guides 152, 156 travel along their respective helical grooves, they in turn force non-magnetic fourth lens 150 to translate in an axial direction within interior chamber 90. As non-magnetic fourth lens 140 translates axially, non-magnetic guides 152, 156 also move axially, maintaining their axial position relative to non-magnetic fourth lens 150.

Figure 12:
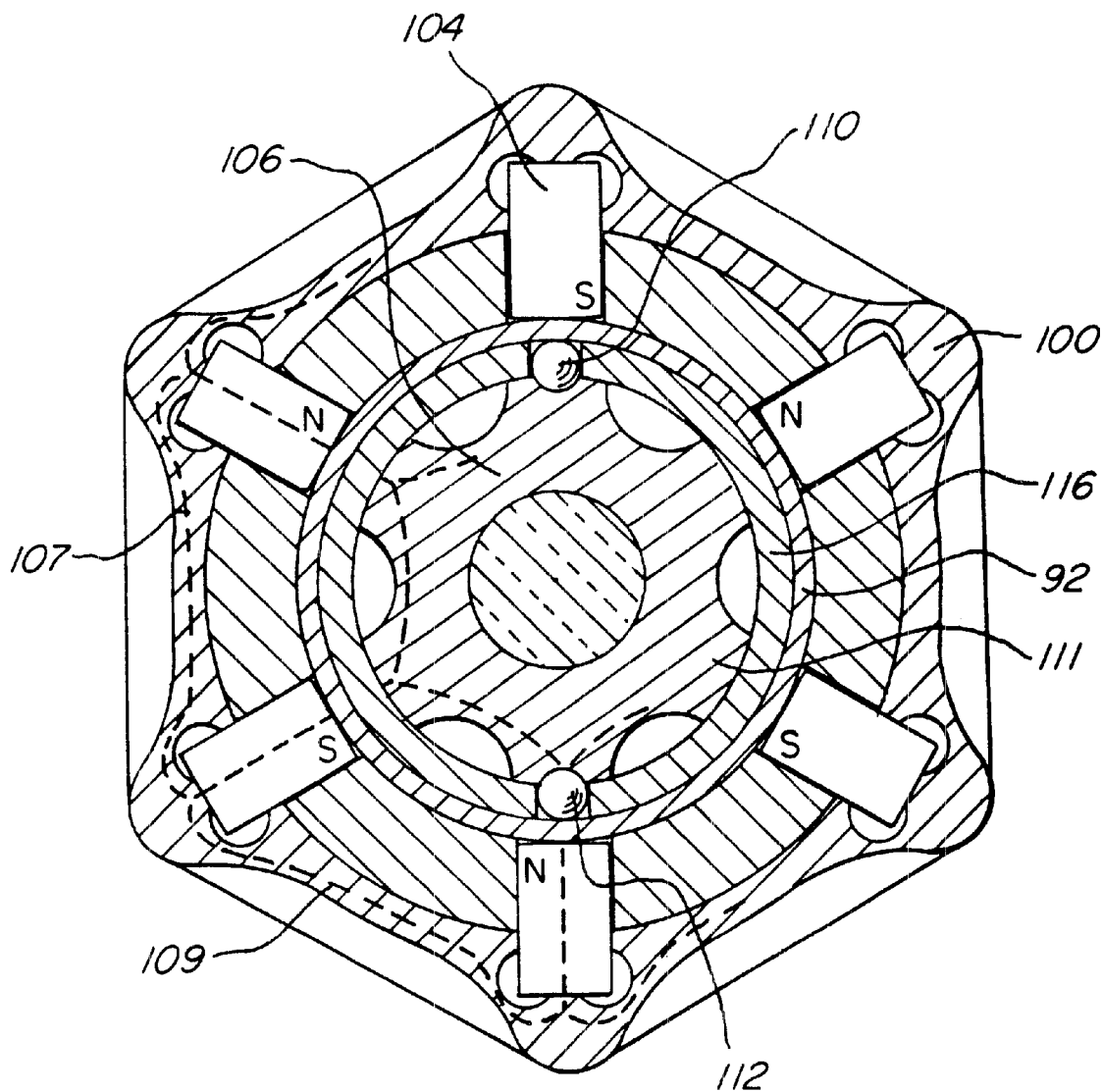
FIG. 12 is a cross-sectional end view of the third embodiment shown in FIG. 10.

When the device is in operation a first magnetic connection exists between external magnets 104 in first adjuster 100 and magnetic first lens 106 (as depicted by dashed lines 107 and 109 of FIG. 12). Accordingly, when first adjuster 100 is moved, the movement of magnetic first lens 106 is similar to the movement described in the first embodiment when lens 28 is moved by adjuster 24. First lens 106 acts as a focusing lens. A second magnetic connection also exists between external magnets 108 in second adjuster 102 and magnetic second lens 128 (as depicted by dashed lines 158 and 160 of FIGS. 13 and 14). Accordingly, when second adjuster 102 is moved, the magnetic second lens 128 also moves, similar to the movement described in the second embodiment when lens 50 is moved by adjuster 64. The rotation of magnetic second lens 128, in turn rotates both non-magnetic third lens 140 and fourth lens 150 axially as dictated by helical groves 120 and 122, similar to the movement described in the second embodiment when lens 52 is moved by adjuster 64. The arrangement of second lens 128, third lens 142, and fourth lens 150 forms a zoom portion of the present embodiment. This allows the operator of the device to zoom in or out of any images transmitted by the endoscope by rotating second "zoom" adjuster 102 in the appropriate direction.

As previously described in the first embodiment, without friction or tension being provided against external adjusters 100, 102, the desired focus or zoom setting (lens positions) of the device would be inadvertently lost due to further handling and movement of the device. Friction or tension against the external adjuster is provided by tensioners preferably pliable o-rings, similar to o-rings 30 and 31 in FIG. 3. The pliable o-rings have a sufficient diameter, that allows for deformation of the o-ring, which in turn provides adequate tension to hold the adjuster in place between adjustments while also allowing ease of rotation by hand. Moreover, the pliable o-rings hold the adjuster parallel to sleeve during rotation of the adjuster. Various other materials and tension producing methods could be used to provide the desired balance between tension and ease of rotation of the adjuster. Such materials and methods that could be used are, but not limited to, metal bushings, pins and grooves, and ball bearings and raceways, and the like.

Continuous rotation of first and second adjusters 100, 102 and consequent unwanted lens rotation can be prevented by stops in the present embodiment using stops similar to those described in the first embodiment. For example, in addition to the use of a first stop similar to the stop described in the first embodiment with first adjuster 100, a second stop formed by using a stop groove in the distal end of sleeve 92 in conjunction with stop tabs formed on adjuster 102 could also be used.

Figure 15:
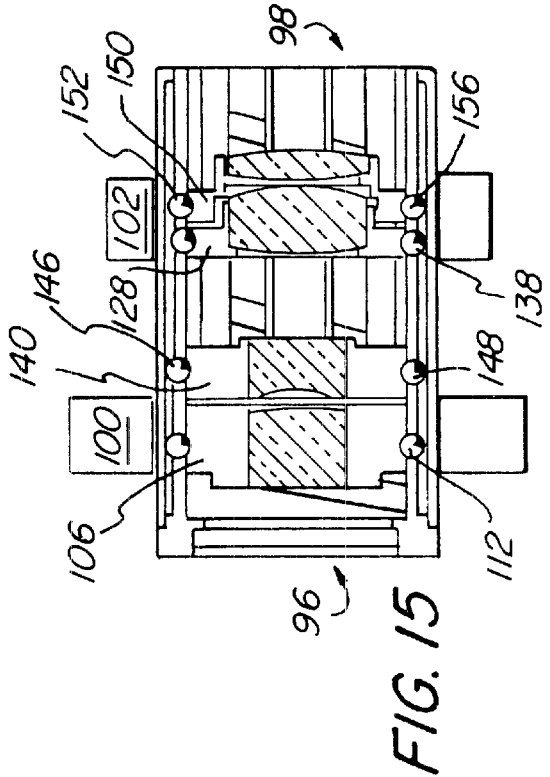
FIG. 15 is a cross-sectional side view of the third embodiment shown in FIG. 10 showing the lens in a first position.
Figure 16:
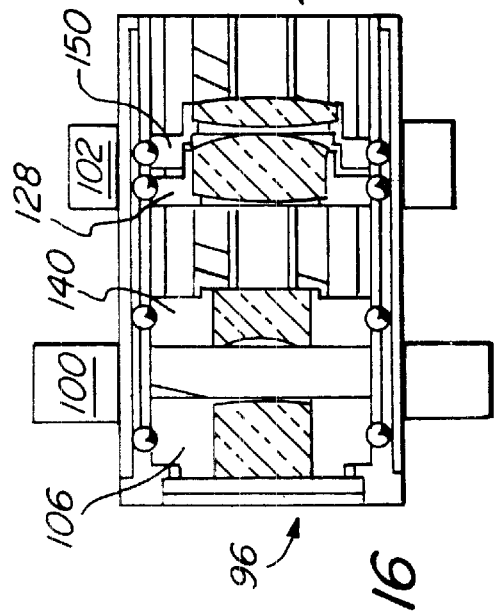
FIG. 16 is a cross-sectional side view of the third embodiment shown in FIG. 10 showing the lens in a second position.

The relative movement of the lenses, due to rotation of first and second adjusters 100, 102, is illustrated by the drawings in FIGS. 15, 16, 17 and 18. FIG. 15 shows a starting position for the four lenses 106, 128, 140, 150 where first lens 106 is in its most distal position 96 98 and third and fourth lens 140, 150 are in their most proximal position 96. Viewing the device from the proximal end 96, as first adjuster 100 is rotated counterclockwise, it will cause first lens 106 to rotate counterclockwise and translate along the center axis of the device towards the proximal end 96 of the device. As first adjuster 100 continues to rotate, first lens 106 will continue to travel forward towards proximal end 96 of the device until it reaches its most proximal position as shown in FIG. 16. The second, third and fourth lens operate independently from first adjuster 100 and, therefore, do not translate axially during the translation of first lens 106, unless adjuster 102 is rotated.

Figure 17:
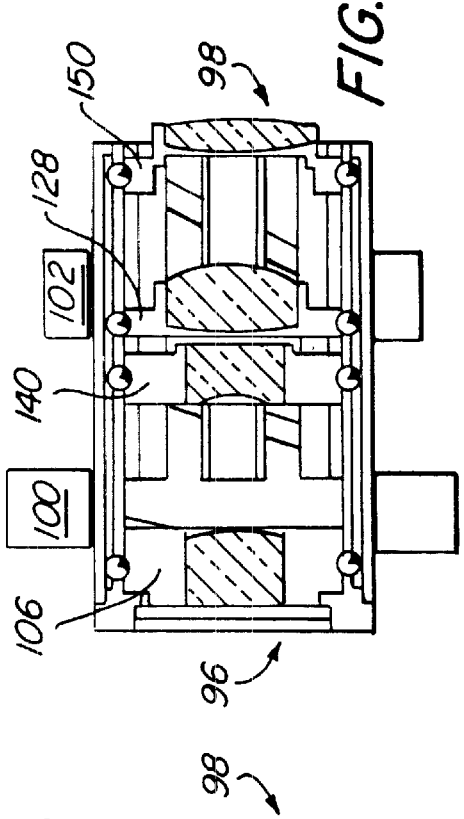
FIG. 17 is a cross-sectional side view of the third embodiment shown in FIG. 10 showing the lens in a third position.

Referring to FIG. 16 to show the relative starting position of the four lenses and viewing the device from the proximal end 96, as second adjuster 102 is rotated clockwise, it will cause ferromagnetic second lens 128 to rotate without translating axially. The fingers that extend proximally and distally from the second lens will in turn cause third and fourth non-magnetic lens 140, 150 to rotate and translate axially within the device towards distal end 98, until third and fourth lens 140, 150 reach their most distal position as shown in FIG. 17. The first lens operates independently from the second adjuster and, therefore, does not translate axially during the rotation and translation of the second, third and fourth lenses.

Figure 18:
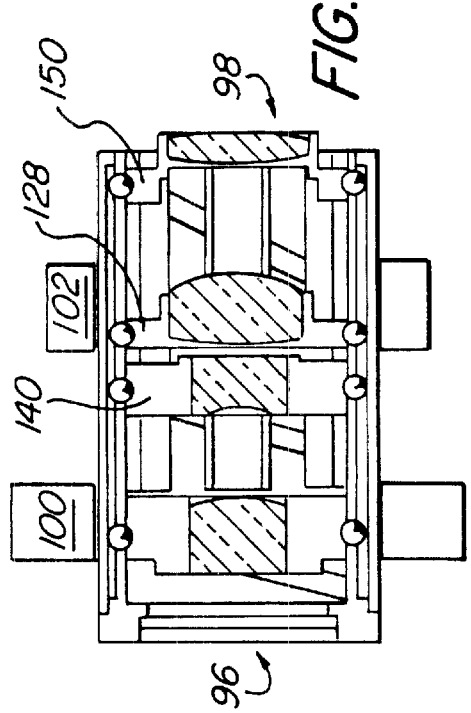
FIG. 18 is a cross-sectional side view of the third embodiment shown in FIG. 10 showing the lens in a fourth position.

Using FIG. 17 as the relative starting position for the four lens and viewing the device from the proximal end 96, as first adjuster 100 is rotated clockwise, it will cause first lens 106 to rotate clockwise and translate along the axis of the device towards the distal end 98 of the device until it is in its most distal position as shown in FIG. 18. Finally, starting with FIG. 18, the operator of the device would only need to rotate second adjuster 102 counterclockwise, causing the third and fourth lens 140, 150 to translate along the axis of the device towards the proximal end 96 of the device until third and fourth lens 140, 150 reach their most proximal position as shown in FIG. 15. It can be seen by these figures that the lenses can be adjusted to any position within the device by simply rotating the first or second adjusters in either the clockwise or counterclockwise positions until the desired lens orientation is reached.

The operation of first adjuster 100 is completely independent of the operation of second adjuster 102, meaning that the rotation of first lens will not affect the positioning of second, third or fourth lenses 128, 140, 150. Similarly, rotation of second adjuster 102 will not affect the location of first lens 106. The invention is not limited to the embodiments shown, as various numbers of adjusters could be used. Also, the invention is not limited to the specific axial orientation of the lens shown in the three embodiments. For example, the invention contemplates any arrangement similar to the third embodiment where the second, third and fourth lens could be positioned axially proximal to first lens 106. Similarly, the invention would cover any axial arrangement of multiple lenses.

This invention is not limited to endoscopic video cameras or endoscopic devices but could be used in any device where lenses must be repositioned for focus and zoom optimization.

What is claimed is:

1. A focusing device comprising:

a first sleeve;

a second sleeve fixedly mounted within said first sleeve, said second sleeve having a groove defining a path of movement;

a lens mounted within said second sleeve, said lens having a first magnetizable portion;

an adjuster mounted for movement about said first sleeve, said adjuster including a second magnetizable portion; and a non-magnetic guide connected to said lens and positioned in said groove such that when said adjuster is moved about said first sleeve, said second magnetizable portion causes said lens to move via a magnetic interaction between said first magnetizable portion and said second magnetizable portion while said guide maintains its axial position relative to said lens.

2. The device of claim 1 wherein a stop connected to said adjuster prevents movement of said adjuster.

3. The device of claim 1 wherein said lens is at least partially comprised of stainless steel.

4. The device of claim 1 wherein said second magnetizable portion is a magnet.

5. The device of claim 4 wherein said magnet is comprised of SmCo.

6. The device of claim 1 wherein said first magnetizable portion is a magnet.

7. The device of claim 6 wherein said magnet is comprised of SmCo.

8. The device of claim 1 wherein said non-magnetic guide is a ball.

9. The device of claim 1 wherein said first sleeve at least partially defines a sealed chamber.

10. The device of claim 1 wherein a tensioner connected to said adjuster holds said adjuster in place.

* * * * *